US010214797B2

(12) United States Patent
Xu et al.

(10) Patent No.: US 10,214,797 B2
(45) Date of Patent: Feb. 26, 2019

(54) METHOD FOR PRODUCTION AND IDENTIFICATION OF WEYL SEMIMETAL

(71) Applicant: TRUSTEES OF PRINCETON UNIVERSITY, Princeton, NJ (US)

(72) Inventors: Suyang Xu, Plainsboro, NJ (US); Ilya Belopolski, New Canaan, CT (US); Nasser Alidoust, Brooklyn, NY (US); Madhab Neupane, Orlando, FL (US); Shuang Jia, Beijing (CN); M. Zahid Hasan, Princeton, NJ (US)

(73) Assignee: TRUSTEES OF PRINCETON UNIVERSITY, Princeton, NJ (US)

(*) Notice: Subject to any disclaimer, the term of this patent is extended or adjusted under 35 U.S.C. 154(b) by 0 days.

(21) Appl. No.: 15/352,279

(22) Filed: Nov. 15, 2016

(65) Prior Publication Data
US 2017/0138844 A1    May 18, 2017

Related U.S. Application Data

(60) Provisional application No. 62/255,790, filed on Nov. 16, 2015.

(51) Int. Cl.
| C04B 35/515 | (2006.01) |
| G01N 23/2273 | (2018.01) |
| C22C 1/05 | (2006.01) |
| C22C 29/00 | (2006.01) |
| C22C 1/00 | (2006.01) |

(Continued)

(52) U.S. Cl.
CPC ............ *C22C 1/058* (2013.01); *C04B 35/515* (2013.01); *C04B 35/5154* (2013.01); *C22C 1/007* (2013.01); *C22C 29/00* (2013.01); *C30B 25/00* (2013.01); *C30B 29/10* (2013.01); *G01N 23/2273* (2013.01); *C04B 2235/3251* (2013.01)

(58) Field of Classification Search
CPC ......... H01L 49/003; G01J 1/4029; G01J 1/44; G01J 2001/4446; C04B 2235/3251; C04B 35/515; C04B 35/5154; C22C 1/007; C22C 1/058; C22C 29/00; C30B 25/00; C30B 29/10; G01N 23/2273
See application file for complete search history.

(56) References Cited

U.S. PATENT DOCUMENTS

2005/0110108 A1* 5/2005 Patel .................. G02B 6/12004
257/453

OTHER PUBLICATIONS

Li et al., "Weyl Semimetal TaAs: Crystal Growth, Morphology, and Thermodynamics," American Chemical Society Crystal Growth & Design, published Feb. 8, 2016, pp. 1172-1175.

* cited by examiner

*Primary Examiner* — David P Porta
*Assistant Examiner* — Faye Boosalis
(74) *Attorney, Agent, or Firm* — MH2 Technology Law Group LLP (57) ABSTRACT

Disclosed is a method for producing and identifying a Weyl semimetal. Identification is enabled via a combination of the vacuum ultraviolet (low-photon energy) and soft X-ray (SX) angle resolved photoemission spectroscopy (ARPES). Production generally requires providing high purity raw materials, creating a mixture, heating the mixture in a container at a temperature sufficient for thermal decomposition of an impurity while preventing the possible reaction between the side walls of the container and the raw materials, depositing the resulting compound and a transfer agent onto the bottom surface of the ampule, differentially heating the ampule, and allowing a chemical vapor transport reaction to complete.

19 Claims, 7 Drawing Sheets

(51) Int. Cl.
*C30B 29/10* (2006.01)
*C30B 25/00* (2006.01)

METHOD FOR PRODUCTION AND IDENTIFICATION OF WEYL SEMIMETAL

CROSS REFERENCE TO RELATED APPLICATIONS

This application claims priority to U.S. Provisional Patent Application Ser. No. 62/255,790 filed on Nov. 16, 2015, which is hereby incorporated by references in its entirety.

FIELD

Weyl fermions have long been known in quantum field theory, but previously have not been observed as a fundamental particle in nature. Recently, it was understood that a Weyl fermion can emerge as a quasiparticle in certain crystals, Weyl fermion semimetals. A Weyl semimetal is a crystal which hosts Weyl fermions as emergent quasiparticles and admits a topological classification that protects Fermi arc surface states on the boundary of a bulk sample. This unusual electronic structure has deep analogies with particle physics and leads to unique topological properties. This unusual electronic structure also leads to difficulties in identifying Weyl semimetals.

Despite being a gapless metal, a Weyl semimetal is characterized by topological invariants, broadening the classification of topological phases of matter beyond insulators. Specifically, Weyl fermions at zero energy correspond to points of bulk band degeneracy, Weyl nodes, which are associated with a chiral charge that protects gapless surface states on the boundary of a bulk sample. These surface states take the form of Fermi arcs connecting the projection of bulk Weyl nodes in the surface Brillouin zone (BZ). A band structure like the Fermi arc surface states would violate basic band theory in an isolated two-dimensional system and can only arise on the boundary of a three-dimensional sample, providing a dramatic example of the bulk-boundary correspondence in a topological phase. In contrast to topological insulators where only the surface states are interesting, a Weyl semimetal features unusual band structure in the bulk and on the surface. The Weyl fermions in the bulk are predicted to provide a condensed matter realization of the chiral anomaly, giving rise to a negative magnetoresistance under parallel electric and magnetic fields, unusual optical conductivity, non-local transport and local non-conservation of ordinary current. At the same time, the Fermi arc surface states are predicted to show novel quantum oscillations in magneto-transport, as well as unusual quantum interference effects in tunneling spectroscopy.

SUMMARY

In accordance with examples of the present disclosure, a method of producing a Weyl semimetal is provided. The method comprises selecting a pair of materials from the group consisting of: tantalum (Ta), arsenide (As), niobium (Nb), and phosphide (P), wherein each of the pair of materials is in powder form and has an initial purity of at least 99.9%; heating the pair of selected materials to form a polycrystalline compound; sealing the polycrystalline compound and a transfer agent in a first end of a closed ampule; and heating the closed ampule to a first temperature at the first end and to a second temperature at a second end to produce a temperate gradient along a length of the closed ampule to grow the Weyl semimetal via a chemical vapor transport (CVT) reaction, wherein the first temperature is lower than the second temperature.

In some examples, the heating the pair of selected materials, further comprises depositing the pair of materials into a container composed of silica; evacuating the container in vacuum; heating the container except where the two materials are located to reduce bound water from an inner wall of the container; and fluxing and evacuating the container with argon gas of purity of about 99.999% and sealing the container with an inner residue pressure less than 1 Pa.

In some examples, the method further comprising, subsequent to the sealing the container, heating the container at a third temperature for a first time period and then heating the container at a fourth temperature that is higher than the third temperature for a second time period.

In some examples, the fourth temperature is chosen to be high for thermal decomposition of impurities while preventing possible reaction between the inner wall of the container and one or more of the two materials.

In some examples, the third temperature is about 873K and the first time period is about 36 hours, the container is heated to the fourth temperature of about 1323K over a 50 hours, and kept at the fourth temperature at the second time period of 36 hours.

In some examples, the transfer agent is one or more of: $SnI_4$ and $TeI_4$.

In some examples, a mass of the transfer agent is between approximately 15% and 30% of a mass of the pair of materials.

In some examples, the CVT occurs over about 7 days.

In some examples, the first temperature is about 1073K and the second temperature is about 1273K.

In accordance with examples of the present disclosure a method of producing a TaAs Weyl semimeta is provided. The method comprises providing Ta powder and As powder, wherein each of the Ta powder and the As powder has an initial purity of at least 99.9%; heating the Ta powder and the As powder to form a polycrystalline TaAs compound, wherein heating eliminates a presence of TaAs2; sealing the polycrystalline TaAs compound and a transfer agent in a first end of a closed ampule, wherein the transfer agent is one or more of: $SnI_4$ and $TeI_4$; and heating the closed ampule to about 1073K at the first end and to about 1273K at a second end to produce a temperate gradient along a length of the closed ampule to grow the TaAs Weyl semimetal via a CVT reaction.

In some examples, heating the Ta and As, the method further comprises depositing the Ta powder and the As powder into a container composed of silica; evacuating the container in vacuum; heating the container except where the Ta powder and the As powder are located to reduce bound water from an inner wall of the container; and fluxing and evacuating the container with argon gas of purity of about 99.999% and sealing the container with an inner residue pressure less than 1 Pa.

In some examples, the method further comprises, subsequent to the sealing the container, heating the container to about 873K for about 36 hours and then heating the container to about 1323K over 50 hours and kept at about 1323K for about 36 hours.

In accordance with examples of the present disclosure, a method of identifying a Weyl semimetal is provided. The method comprises directing vacuum ultraviolet (UV) radiation from an UV radiation source and soft x-ray radiation from an x-ray radiation source onto a material; detecting a crescent feature and band dispersions at representative momentum space cuts; analyzing, using a hardware processor, the band dispersions to determine that the band dispersions moving in a same direction as energy levels from one or more the of UV radiation source and the x-ray radiation source are varied; and classifying the material as a Weyl semimetal based on the analyzing.

In some examples, the UV radiation source uses low-photon energy angle-resolved photoemission spectroscopy ("ARPES").

In some examples, the analyzing further comprises tuning free parameters of a surface calculation to obtain a calculated surface Fermi surface, wherein a Weyl semimetal exists if the calculated surface Fermi surface reproduces data from the ARPES.

In some examples, the UV radiation is between about 10 eV and about 100 eV and the soft x-ray radiation is between about 300 eV and about 1000 eV.

In some examples, the analyzing further comprises mapping a $k_x$-$k_z$ Fermi surface using the ARPES; identifying a bulk band structure; selecting an incident photo energy that corresponds to the k-space location of nodes located away from a $k_x$ ($2\pi/a$) mirror plane; mapping a $k_x$-$k_y$ Fermi surface; and identifying a Fermi point comprising a dispersive cone away from $k_x$ or $k_y$ axes; wherein a Weyl semimetal exists if the Fermi point away from the $k_x$ or $k_y$ axes exist.

In some examples, the classifying further comprises comparing a location of the Fermi point with bulk calculations, wherein a Weyl semimetal exists if the location of the Fermi point is consistent with bulk calculations.

In accordance with examples of the present disclosure, a method of producing a Weyl semimetal is provided. The method includes producing a polycrystal, providing an appropriate ampule, and growing the crystal via a chemical vapor transport reaction. Producing a polycrystal requires providing high purity raw materials, creating a mixture, and heating the mixture in a container at a temperature sufficient for thermal decomposition of an impurity while preventing the possible reaction between the side walls of the container and the raw materials. An appropriate ampule is then produced. Growing the crystal requires depositing the polycrystal and an appropriate transfer agent onto the bottom surface of the ampule, differentially heating the ampule, and allowing a chemical vapor transport reaction to complete.

In accordance with examples of the present disclosure, a method of identifying Weyl semimetals is provided. The method includes using low-photon energy ARPES to single out a crescent feature and show band dispersions at representative momentum space cuts, wherein a Weyl semimetal exists if the band dispersions at representative momentum spacecuts moving in the same direction as the energy levels are varied. In some examples, the method further includes tuning the free parameters of a surface calculation to obtain a calculated surface Fermi surface, wherein a Weyl semimetal exists if the calculated surface Fermi surface reproduces the low-photon energy ARPES data.

In accordance with examples of the present disclosure, a method of identifying bulk Weyl nodes is provided. The method includes using soft x-ray ARPES to map a $k_x$-$k_z$ Fermi surface; identifying a bulk band structure; selecting an incident photo energy that corresponds to the k-space location of nodes located away from a $k_z$=0 plane; mapping a $k_x$-$k_y$ Fermi surface; and identifying a Fermi point comprising a dispersive cone away from $k_x$ or $k_y$ axes, wherein a Weyl semimetal exists if the Fermi point away from the $k_x$ or $k_y$ axes exist. In some examples, the method further includes comparing the location of the Fermi point with bulk calculations, wherein a Weyl semimetal exists if the location of the Fermi point is consistent with bulk calculations.

In accordance with examples of the present disclosure, a method of identifying Weyl semimetals is provided. The method includes using low-photon energy ARPES to single out a crescent feature and show band dispersions at representative momentum space cuts, wherein a Weyl semimetal exists if the band dispersions at representative momentum space-cuts moving in the same direction as the energy levels are varied, and verifying the existence of the Weyl semimetal by a method including using soft x-ray ARPES to map a $k_x$-$k_z$ Fermi surface; identifying a bulk band structure; selecting an incident photo energy that corresponds to the k-space location of nodes located away from a $k_z$=0 plane; mapping a $k_x$-$k_y$ Fermi surface; and identifying a Fermi point comprising a dispersive cone away from $k_x$ or $k_y$ axes; wherein a Weyl semimetal exists if the Fermi point away from the $k_x$ or $k_y$ axes exist.

BRIEF DESCRIPTION OF THE FIGURES

FIGS. 2A-2H show a crystal structure and electronic structure of TaAs, according to examples of the present disclosure.

FIGS. 3A-3G show observations of topological Fermi arc surface states on the (001) surface of TaAs, according to examples of the present disclosure. FIG. 3E shows the same Fermi surface map as in FIG. 3B. The dotted lines define the −space direction for Cuts I and II. The numbers 1-6 note the Fermi crossings that are located on Cuts I and II. The arrows 315 show the evolution of the constant energy contours as one varies the binding energy, which is obtained from the dispersion maps in FIGS. 3C and 3D.

FIGS. 4A-4J show observations of bulk Weyl Fermion cones and Weyl nodes in TaAs, according to examples of the present disclosure.

FIGS. 5A-5E show surface-bulk correspondence and the topologically nontrivial state in TaAs, according to examples of the present disclosure.

DETAILED DESCRIPTION

Reference will now be made in detail to the present embodiments, examples of which are illustrated in the accompanying drawings. Wherever possible, the same reference numbers will be used throughout the drawings to refer to the same or like parts.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5. In certain cases, the numerical values as stated for the parameter can take on negative values. In this case, the example value of range stated as "less that 10" can assume negative values, e.g. −1, −2, −3, −10, −20, −30, etc.

The following embodiments are described for illustrative purposes only with reference to the figures. Those of skill in the art will appreciate that the following description is exemplary in nature, and that various modifications to the parameters set forth herein could be made without departing from the scope of the present invention. It is intended that the specification and examples be considered as examples only. The various embodiments are not necessarily mutually exclusive, as some embodiments can be combined with one or more other embodiments to form new embodiments.

Figure 1:
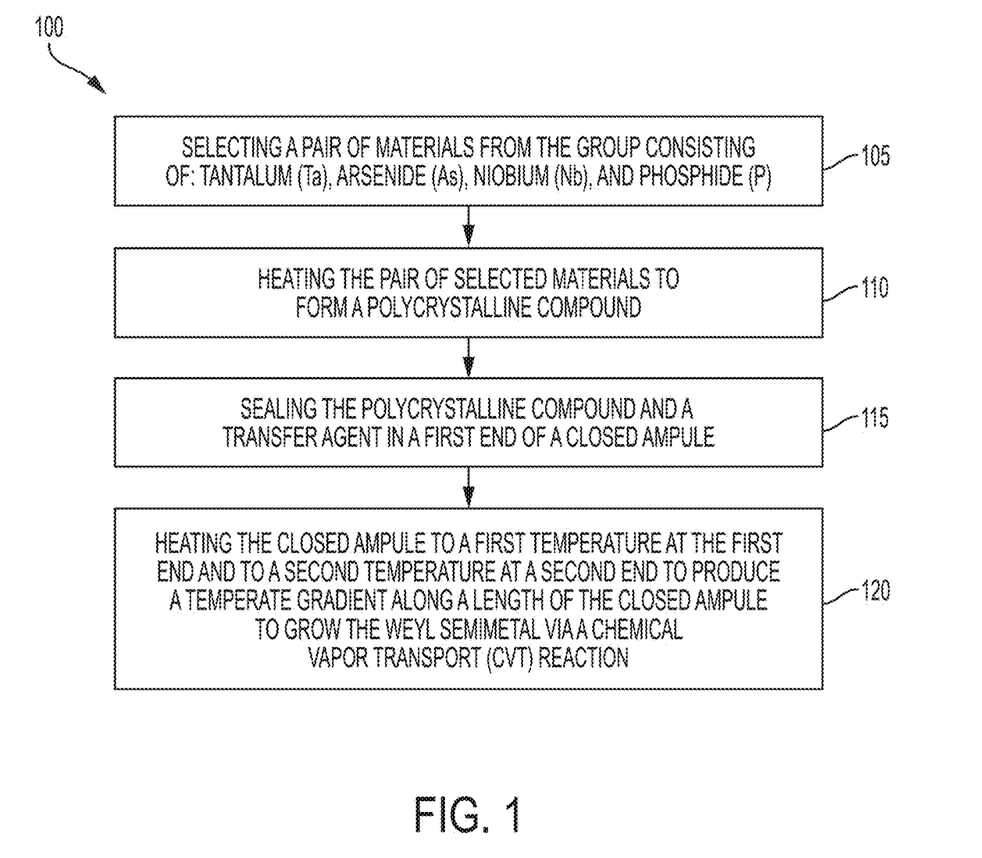
FIG. 1 shows a method of producing a Weyl semimetal, according to examples of the present disclosure.

FIG. 1 shows a method for production of a Weyl semimetal 100, according to examples of the present disclosure. The Weyl semimetal can be composed of tantalum arsenide (TaAs), niobium arsendide (NbAs), tantalum phosphide (TaP) or niobium phosphide (NbP). At 105, a pair of materials are selected from the group consisting of: tantalum (Ta), arsenide (As), niobium (Nb), and phosphide (P). Each of the pair of materials is selected in powder form and has an initial purity of at least 99.9%.

At 110, the pair of selected materials are heated to form a polycrystalline compound. For example, high-purity elements appropriate for production of a Weyl semimetal can be measured and can then be placed into tubes comprised of an appropriately selected material, such as silica. Next, the tubes containing the mixtures can be evacuated in vacuum, and heated, except the part of the tube containing the selected elements to reduce bounded water inside the inner walls of the tubes. The tubes can then fluxed and evacuated with high purity argon (99.999%) or other appropriate gas, such as an inert gas (He, Ne, Ar, Kr), and sealed with the inner residue pressure less than 1 Pa. The tubes can then heated in an appropriate furnace, such as an electric furnace at moderately high temperature for an initial period. In one example involving Ta and As, this was done at 873K for 36 hours, in order to prevent the possible explosion of over-evaporate arsenic vapor. The tubes can be then slowly heated to a highest temperature and over a period of time, and then held at that temperature for an additional time period. The highest temperature is chosen to be sufficiently high for thermal decomposition of impurities while preventing the possible reaction between the silica inner wall and tantalum.

At 115, the polycrystalline compound and a transfer agent can be sealed in a first end of a closed ampule or other sealed vial. For example, the ampule is capable of being used for a chemical vapor transport reaction. The ampules can be long and silica-based. One skilled in the art will recognize that many variations of ampules can be used.

At 120, the closed ampule is heated to a first temperature at the first end and to a second temperature that is higher than the first temperature at a second end to produce a temperate gradient along a length of the closed ampule to grow the Weyl semimetal via a chemical vapor transport (CVT) reaction. For example, the polycrystalline compound is first placed on the bottom of one ampule along with a small quantity of an appropriate transfer agent. In some examples, the polycrystalline compound is placed such that the polycrystalline crystalline compound only contacts the bottom of the ampule. A transfer agent is provided in the ampule having a mass of transfer agent between about 15% and about 30% of the mass of the polycrystalline compound that is added into the ampule. The transfer agent can be $SnI_4$ and/or $TeI_4$. Then, the ampule is evacuated in vacuum, and heated, except the part containing the polycrystalline compound for reducing bounded water inside the inner silicon wall. Then the ampule is fluxed and evacuated with high purity argon (99.999%) or other appropriate gas, such as an inert gas (He, Ne, Ar, Kr). This process of fluxing and evacuating can be repeated more than one times. In one example, the process is repeated three times. The ampule is then sealed so that the closed ampule has an inner residue pressure of less than about 1 Pa. The closed ampule is then placed in an appropriate furnace having two or more zones that can differentially heat the closed ampule. For example, a zone of the furnace with an end of the closed ampule containing the polycrystalline compound can be set at a first temperature, and another zone near an opposite end of the closed ampule can be set at a temperature that is higher than the first temperature. The chemical vapor transport reaction occurs due to the temperature gradient and produces the single crystal Weyl semimetal. The Weyl semimetal can include various compounds, including but not limited to TaAs, NbAs, TaP and NbP.

EXAMPLE 1

The disclosed method was used to produce a TaAs semimetal. In this example, Ta: 99.98% and As: 99.999% were first accurately weighed with the error less than 0.5 mg, comparing to 4 g total weight. Silica tubes containing the mixtures were then evacuated in vacuum, and heated, except the part containing elements for reducing bounded water inside the inner silicon wall. The tubes were then fluxed and evacuated with high purity argon (99.999%), and sealed with the inner residue pressure less than 1 Pa. The tubes were then heated in an electric furnace at 873K for 36 hours. The tubes were then slowly heated from 873K to 1323K within 50 hours, and kept at 1323K for 36 hours. 1323K was chosen as the highest temperature as it was sufficient for thermal decomposition of the $TaAs_2$ impurity while preventing the possible reaction between the silica inner wall and tantalum. Then, the furnace was shut down and air cooled to room temperature. Following this process produced clean silica inner walls that show no signature of reaction between the tubes and samples. X-ray diffraction showed polycrystalline TaAs was formed with no impurities.

Next, ampules were made from silica tubes. First, the tubes, having inner diameter of 12 mm and outer diameter of 14 mm were cut to 31 cm in length and then sealed on one end. Then the inner side of ampules was washed with ethanol one time, and cleaned by filling with dilute hydrochloric acid and subject to ultrasound for about 15 minutes. After that, the ampules were washed with deionized water 3 times and heated in oven at 393 K for more than 3 hours. All the ampules' opening ends were covered with air-laid papers until being used.

Next, 0.3 g of high quality polycrystalline TaAs, and 60 mg high quality $SnI_4$ as a transfer agent, were placed at the bottom of a silica ampule without any of the TaAs touching other parts of the ampule. Then, the silica ampule was evacuated in vacuum, and heated, except the part containing compounds for reducing bounded water inside the inner silicon wall. Then the ampule was fluxed and evacuated with high purity argon (99.999%), and sealed with an inner residue pressure of less than about 1 Pa. The closed ampule had a total length of about 23 cm and total volume about 26 $cm_3$. The closed ampule was then placed into a three-zone furnace. The end of the closed ampule containing the polycrystalline TaAs was within a first zone and an opposite end of the ampule was in the third zone. The second or middle zone was between the first and third zones. The first zone containing the polycrystalline TaAs was set at 1073K and the middle zone was set as 1273K. The entire chemical vapor transport (CVT) reaction time was 7 days. After the reaction, the furnace was shut down and air cooled. TaAs single crystals were only formed at the middle to the end of the ampule which did not contain the polycrystalline TaAs. The sizes of the single crystals varied from 0.5 mm to 1.5 mm. Typical morphologies were pyramid-like or truncated pyramid-like with square or rectangle face on the truncated top. Near-stoichiometric ratios between Ta and As were observed. The above example was repeated using the same steps, only using a combination of 60 mg high quality $SnI_4$ and 20 mg high quality $TeI_4$ as the transfer agent, with identical results save that the crystals grown with a small amount of $TeI_4$ as the agent were much easier to cleave.

In some examples of the present disclosure, a method for identifying crystals as Weyl semimetals is provided. Using a combination of the vacuum ultraviolet (low-photon energy between about 10 eV and about 100 eV) and soft X-ray (SX) angle-resolved photoemission spectroscopy (ARPES) between about 300 eV and about 1000 eV, the surface and bulk electronic structure of a Weyl semimetal can be systematically and differentially studied. The ultraviolet (low-photon-energy) ARPES measurements, which are highly surface sensitive, demonstrate the existence of the Fermi arc surface states, consistent with our band calculations presented here. Moreover, the SX-ARPES measurements, which are reasonably bulk sensitive, reveal the three-dimensional linearly dispersive bulk Weyl cones and Weyl nodes. Furthermore, by combining the low-photon-energy and SX-ARPES data, the locations of the projected bulk Weyl nodes can be shown to correspond to the terminations of the Fermi arcs within our experimental resolution. These systematic measurements identify a material as a Weyl semimetal.

Experimental realization of a Weyl semimetal in a single crystalline material tantalum arsenide, TaAs, is provided based on experiments conducted by the inventors. Using the combination of the vacuum ultraviolet (low-photon energy between about 10 eV and about 100 eV) and soft X-ray (SX) angle-resolved photoemission spectroscopy (ARPES) between about 300 eV and about 1000 eV, the surface and bulk electronic structure of TaAs has been examined. The ultraviolet (low-photon-energy) ARPES measurements, which are highly surface sensitive, demonstrate the existence of the Fermi arc surface states, consistent with band calculations performed by the inventors that are presented here. Moreover, the SX-ARPES measurements, which are reasonably bulk sensitive, reveal the three-dimensional linearly dispersive bulk Weyl cones and Weyl nodes. Furthermore, by combining the low-photon-energy and SX-ARPES data, the locations of the projected bulk Weyl nodes are shown to correspond to the terminations of the Fermi arcs within the experimental resolution. These systematic measurements demonstrate TaAs as a Weyl semimetal.

Figure 2A:
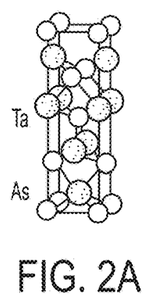
FIG. 2A shows a body-centered tetragonal structure of TaAs, shown as stacked Ta and As layers. The lattice of TaAs does not have space inversion symmetry.
Figure 2B:
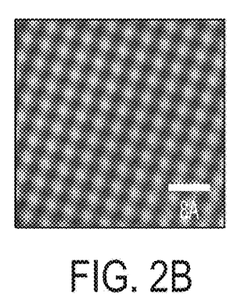
FIG. 2B shows a STM topographic image of TaAs's (001) surface taken at the bias voltage −300 mV, revealing the surface lattice constant.
Figure 2C:
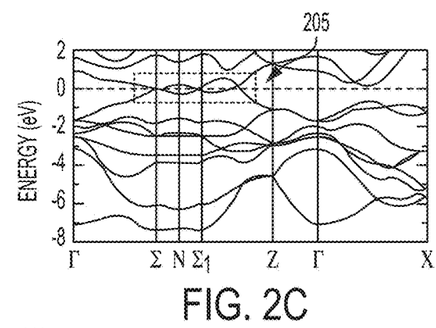
FIG. 2C illustrates a first-principles band structure calculations of TaAs without spin-orbit coupling. The box 205 highlights the locations where bulk bands touch in the BZ.
Figure 2D:
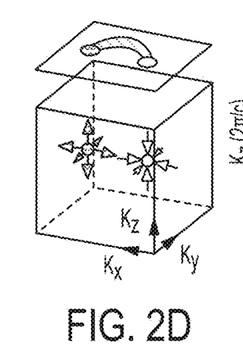
FIG. 2D illustrates of the simplest Weyl semimetal state that has two single Weyl nodes with the opposite (±1) chiral charges in the bulk.
Figure 2E:
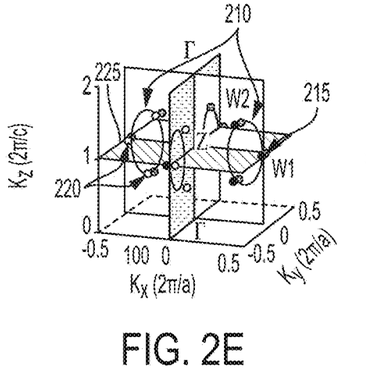
FIG. 2E shows, in the absence of spin-orbit coupling, there are two line nodes on the mirror plane and two line nodes on the mirror plane, denoted by loops 210. In the presence of spin-orbit coupling, each line node reduces into six Weyl nodes, denoted by circles 215 and 220 that show the opposite chiral charges of the Weyl nodes.
Figure 2F:
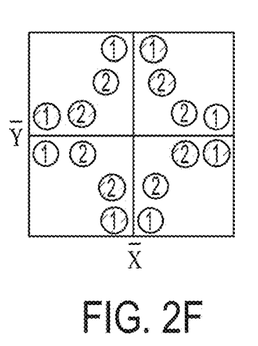
FIG. 2F shows a schematic (not to-scale) showing the projected Weyl nodes and their projected chiral charges.
Figure 2G:
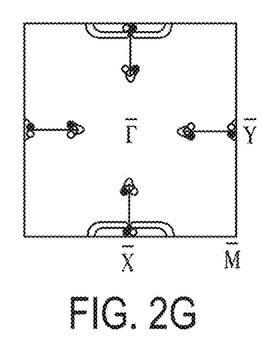
FIG. 2G shows theoretically calculated band structure of the Fermi surface on the (001) surface of TaAs.
Figure 2H:
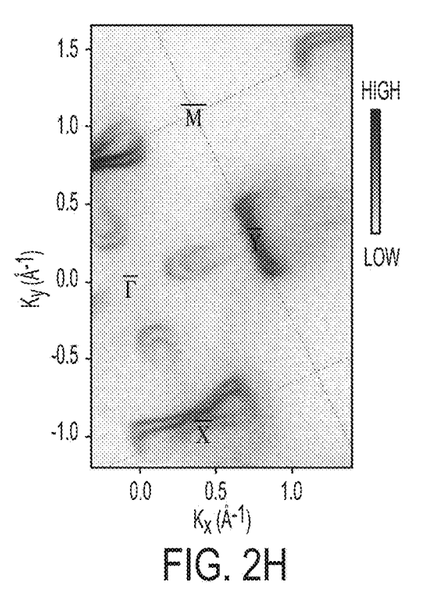
FIG. 2H shows the ARPES measured Fermi surface of the (001) cleaving plane of TaAs. The high symmetry points of the surface BZ are noted.

FIGS. 2A-2H show a crystal structure and electronic structure of TaAs, according to examples of the present disclosure. FIG. 2A shows a body-centered tetragonal structure of TaAs, shown as stacked Ta and As layers. The lattice of TaAs does not have space inversion symmetry. FIG. 2B shows a STM topographic image of TaAs's (001) surface taken at the bias voltage −300 mV, revealing the surface lattice constant. FIG. 2C illustrates a first-principles band structure calculations of TaAs without spin-orbit coupling. The box 205 highlights the locations where bulk bands touch in the BZ. FIG. 2D illustrates of the simplest Weyl semimetal state that has two single Weyl nodes with the opposite (±1) chiral charges in the bulk. FIG. 2E shows, in the absence of spin-orbit coupling, there are two line nodes on the mirror plane and two line nodes on the mirror plane, denoted by loops 210. In the presence of spin-orbit coupling, each line node reduces into six Weyl nodes (small black and white circles). Black and white show the opposite chiral charges of the Weyl nodes. FIG. 2F shows a schematic (not to-scale) showing the projected Weyl nodes and their projected chiral charges. FIG. 2G shows theoretically calculated band structure of the Fermi surface on the (001) surface of TaAs. FIG. 2H shows the ARPES measured Fermi surface of the (001) cleaving plane of TaAs. The high symmetry points of the surface BZ are noted.

TaAs is a semimetallic material that crystalizes in a body-centered tetragonal lattice system (FIG. 2A). The lattice constants are a=3.437 A and c=11.656 A, and the space group is I4$_1$md (#109, C$_{4v}$), as consistently reported in previous structural studies. The crystal consists of interpenetrating Ta and As sub-lattices, where the two sub-lattices are shifted by $$\left(\frac{a}{2}, \frac{a}{2}, \delta\right), \delta \approx \frac{c}{12}.$$

The diffraction data was shown to match well with the lattice parameters and the space group. The scanning tunneling microscopic (STM) topography (FIG. 2B) clearly resolves the (001) square lattice without any obvious defect. From the topography, we obtain a lattice constant a=3.45 A. Electrical transport measurements on TaAs confirmed its semimetallic transport properties and reported negative magnetoresistance suggesting the anomalies due to Weyl fermions.

Figure 3A:
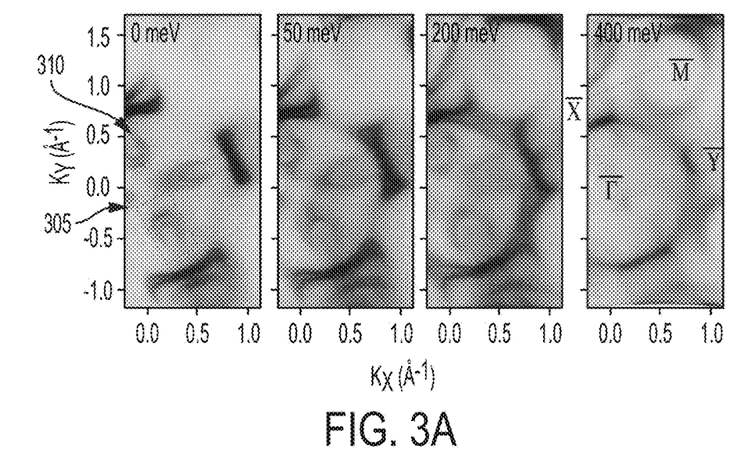
FIG. 3A shows a ARPES Fermi surface map and constant binding energy contours measured using incident photon energy of FIGS. 3B-3G.
Figure 3B:
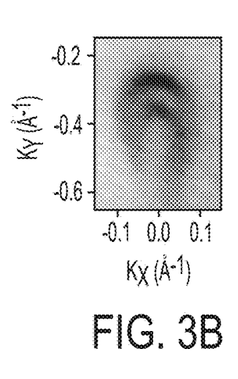
FIG. 3B shows a high-resolution ARPES Fermi surface map of the crescent Fermi arcs. The space range of this map is defined by the box 305 in FIG. 3A.
Figure 3C:
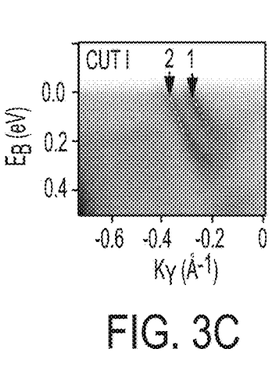
FIGS. 3C and 3D shows energy dispersion maps along Cuts I and II, respectively.
Figure 3D:
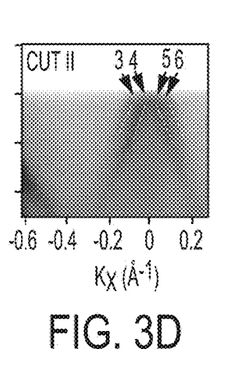
Figure 3E:
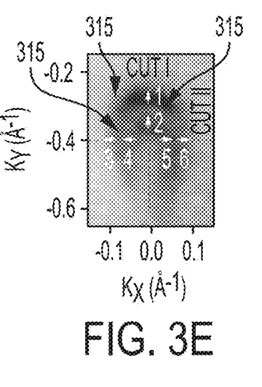
Figure 3F:
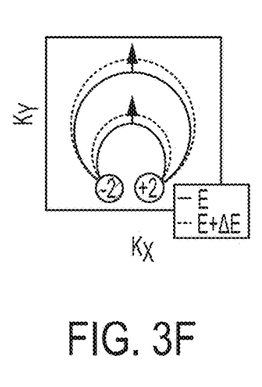
FIG. 3F shows a schematic showing the evolution of the Fermi arcs as a function of energy, which clearly distinguish between two Fermi arcs and a closed contour.
Figure 3G:
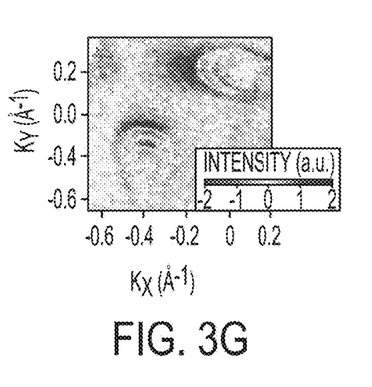
FIG. 3G shows the difference between the constant energy contours at the binding energy and the binding energy, from which one can visualize the evolution of the constant energy contours through space. The range of this map is shown by the dotted box 310 in FIG. 3A.

FIGS. 3A-3G show observations of topological Fermi arc surface states on the (001) surface of TaAs, according to examples of the present disclosure. FIG. 3A shows a ARPES Fermi surface map and constant binding energy contours measured using incident photon energy of FIGS. 3B-3G. FIG. 3B shows a high-resolution ARPES Fermi surface map of the crescent Fermi arcs. The space range of this map is defined by the box 305 in FIG. 3A. FIGS. 3C and 3D shows energy dispersion maps along Cuts I and II, respectively. FIG. 3E shows the same Fermi surface map as in FIG. 3B. The dotted lines define the −space direction for Cuts I and II. The numbers 1-6 note the Fermi crossings that are located on Cuts I and II. The arrows 315 show the evolution of the constant energy contours as one varies the binding energy, which is obtained from the dispersion maps in FIGS. 3C and 3D. FIG. 3F shows a schematic showing the evolution of the Fermi arcs as a function of energy, which clearly distinguish between two Fermi arcs and a closed contour. FIG. 3G shows the difference between the constant energy contours at the binding energy and the binding energy, from which one can visualize the evolution of the constant energy contours through space. The range of this map is shown by the dotted box 310 in FIG. 3A.

Without spin-orbit coupling, calculations show that the conduction and valence bands interpenetrate (dip into) each other to form four 1D line nodes (closed loops) located on the k$_x$ and k$_y$ planes (shown as 210 in FIG. 2E). Upon the inclusion of spin-orbit coupling, each line node loop is gapped out and shrinks into six Weyl nodes that are away from the k$_x$=0 and k$_y$=0 mirror planes (FIG. 2E, circles 215). In calculations performed by the inventors, in total there are 24 bulk Weyl cones, all of which are linearly dispersive and are associated with a single chiral charge of ±1 (FIG. 2E). The 8 Weyl nodes that are located on the plane $$225\left(k_z = \frac{2\pi}{c}\right)$$

as are denoted as W1 and the other 16 nodes that are away from this plane as W2. At the (001) surface BZ (FIG. 2F), the 8 W1 Weyl nodes are projected in the vicinity of the surface BZ edges, X̄ and Ȳ. More interestingly, pairs of W2 Weyl nodes with the same chiral charge are projected onto the same point on the surface BZ. Therefore, in total there are 8 projected W2 Weyl nodes with a projected chiral charge of ±2, which are located near the midpoints of the Γ̄-X̄ and the τ̄-Ȳ lines. Because the ±2 chiral charge is a projected value, the Weyl cone is still linear. The number of Fermi arcs terminating on a projected Weyl node must equal its projected chiral charge. Therefore, in TaAs, two Fermi arc surface states must terminate on each projected W2 Weyl node.

Low-photon-energy ARPES measurements were performed to explore surface electronic structure of TaAs. FIG. 2H presents an overview of the (001) Fermi surface map. Three types of dominant features were observed, namely a crescent-shaped feature in the vicinity of the midpoint of each τ̄-X̄ or τ̄-Ȳ line, a bowtie-like feature centered at the X̄ point, and an extended feature centered at the Ȳ point. The Fermi surface and the constant energy contours were found at shallow binding energies (FIG. 3A) violate the C$_4$ symmetry, considering the features at X̄ and Ȳ points. In the crystal structure of TaAs, where the rotational symmetry is implemented as a screw axis that sends the crystal back into itself after a C$_4$ rotation and a translation by c/2 along the rotation axis, such an asymmetry is expected in calculation. The crystallinity of (001) surface in fact breaks the rotational symmetry. The crescent-shaped features suggest the existence of two arcs and their termination points in k-space seem to coincide with the surface projection of the W2 Weyl nodes. Because the crescent feature consists of two non-closed curves, it can either arise from two Fermi arcs or a closed contour, however, the decisive property that clearly distinguishes one case from the other is the way in which the constant energy contour evolves as a function of energy. As shown in FIG. 3F, in order for the crescent feature to be Fermi arcs, the two non-closed curves have to move (disperse) in the same direction as one varies the energy. ARPES data is provided to show that the crescent features in TaAs indeed exhibit this "co-propagating" property. To do so, a crescent feature is singled out as shown in FIGS. 3B and 3E and show the band dispersions at representative momentum space cuts, Cut I and Cut II, as defined in FIG. 3E. The corresponding E-k dispersions are shown in FIGS. 3C and 3D. The evolution (dispersive "movement") of the bands as a function of binding energy can be clearly read from the slope of the bands in the dispersion maps, and is indicated in FIG. 3E by the arrows 305. It can be seen that the evolution of the two non-closed curves are consistent with the co-propagating property. In order to further visualize the evolution of the constant energy contour throughout $k_x,k_y$ space, the surface state constant energy contours are used at two slightly different binding energies, namely $E_B=0=E_F$ and $E_B=20$ meV. FIG. 3G shows the difference between these two constant energy contours, namely, $\Delta I(k_x,k_y)=I(E_B=20\ \text{meV},k_x,k_y)-I(E_B=0\ \text{meV},k_x,k_y)$, where I is the ARPES intensity. The k-space regions in FIG. 3G that have negative spectral weight correspond to the constant energy contour at $E_B=0$ meV, whereas those regions with positive spectral weight corresponds to the contour at $E_B=20$ meV. Thus one can visualize the two contours in a single $k_x,k_y$ map. The alternating sequence for each crescent feature in FIG. 3G shows the co-propagating property, consistent with FIG. 3F. Furthermore, it is noted that there are two crescent features, one located near the $k_x=0$ axis and the other near the $k_y=0$ axis, in FIG. 3G. The fact that the co-propagating property are observed for two independent crescent features which are rotated 90° with respect to each other further shows that this observation is not due to artifacts, such as a k misalignment while performing the subtraction. The above systematic data reveal the existence of Fermi arcs on the (001) surface of TaAs. Just like one can identify a crystal as a topological insulator by observing an odd number of Dirac cone surface states, the data presented here is sufficient to identify TaAs as a Weyl semimetal because of bulk-boundary correspondence in topology. Theoretically, the co-propagating property of the Fermi arcs is unique to Weyl semimetals because it arises from the nonzero chiral charge of the projected bulk Weyl nodes, which in this case is ±2. Therefore, this property distinguishes the crescent Fermi arcs not only from any closed contour but also from the double Fermi arcs in Dirac semimetals because the bulk Dirac nodes do not carry any net chiral charges. After observing the surface electronic structure containing Fermi arcs in the ARPES data, the free parameters of the surface calculation are able to be refined to obtain a calculated surface Fermi surface that reproduces and explains the ARPES data (FIG. 2G). This serves as a cross-check that the data and interpretation are self consistent. Specifically, the surface calculation indeed also reveals the crescent Fermi arcs that connect the projected W2 Weyl nodes near the midpoints of each $\bar{\tau}$-$\bar{X}$ or $\bar{\tau}$-$\bar{Y}$ line (FIG. 2G). In addition, the calculation shows the bowtie surface states centered at the $\bar{X}$ point, also consistent with the ARPES data. According to the calculation, these bowtie surface states are in fact Fermi arcs (26) associated with the W1 Weyl nodes near the BZ boundaries. However, the ARPES data cannot resolve the arc character since the W1 Weyl nodes are too close to each other in momentum space compared to the experimental resolution. Additionally, it is noted that the agreement between the ARPES data and the surface calculation upon the contour at the $\bar{Y}$ point can be further improved by fine-optimizing the surface parameters. In order to establish the topology, it is not necessary for the data to have a perfect correspondence with the details of calculation because some changes in the choice of the surface potential allowed by the free parameters do not change the topology of the materials, as is the case in topological insulators. In principle, Fermi arcs can coexist with additional closed contours in a Weyl semimetal just as Dirac cones can coexist with additional trivial surface states in a topological insulator. Particularly, establishing one set of Weyl Fermi arcs is sufficient to prove a Weyl semimetal. This is achieved by observing the crescent Fermi arcs as is shown here by the ARPES data in FIGS. 3A-3G, which is further consistent with the surface calculations.

Figure 4A:
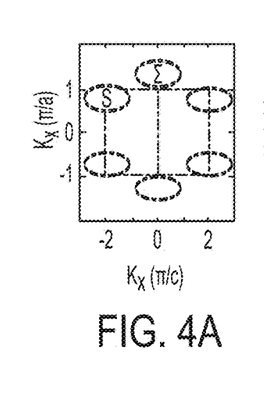
FIGS. 4A and 4B shows first principles calculated and ARPES measured $k_z$-$k_x$ Fermi surface maps at $k_y$=0, respectively.
Figure 4B:
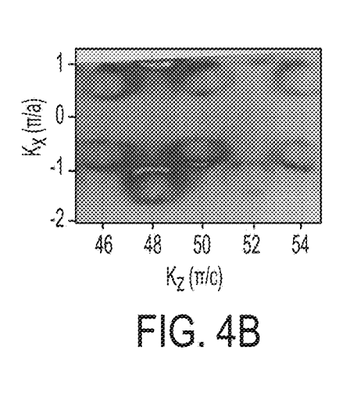
Figure 4C:
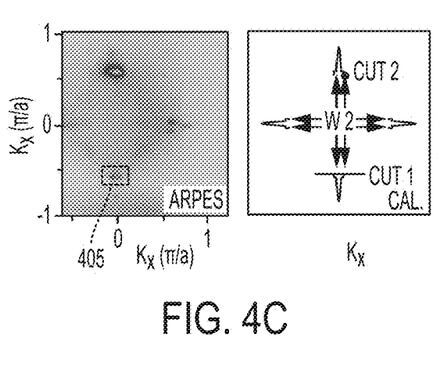
FIG. 4C shows ARPES measured and first-principles calculated $k_x$-$k_y$ Fermi surface maps at the $k_z$ value that corresponds to the W2 Weyl nodes. The dotted line defines the k-space cut direction for Cut 1, which goes through two nearby W2 Weyl nodes along the kA direction. The black cross defines Cut 2, which means that the $k_z$,$k_y$ values are fixed at the location of a W2 Weyl node and one varies the $k_z$ value.
Figure 4D:
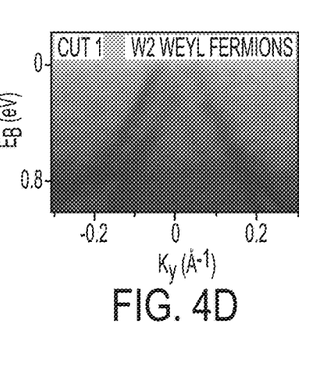
FIG. 4D shows an ARPES E-$k_y$ dispersion map along the Cut 1 direction, which clearly shows the two linearly dispersive W2 Weyl cones.
Figure 4E:
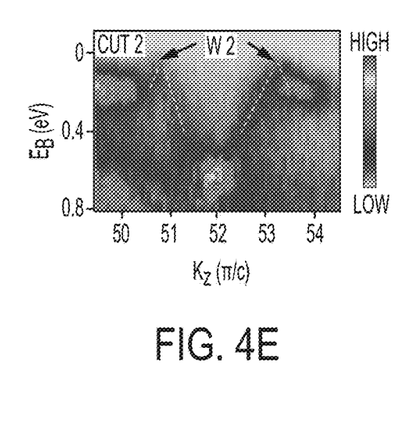
FIG. 4E shows an ARPES E-$k_z$ dispersion map along the Cut 2 direction, showing that the W2 Weyl cone also disperses linearly along the out-of-plane $k_z$ direction.
Figure 4F:
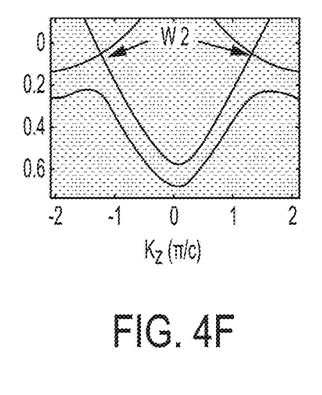
FIG. 4F shows a first-principles calculated E-$k_z$ dispersion that corresponds to the Cut 2 shown in FIG. 4E.
Figure 4G:
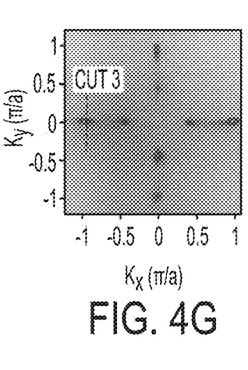
FIG. 4G shows an ARPES measured $k_w$-$k_y$ Fermi surface maps at the $k_z$ value that corresponds to the W1 Weyl nodes. The dotted line defines the k-space cut direction for Cut 3, which goes through the W1 Weyl nodes along the $k_y$ direction.
Figure 4H:
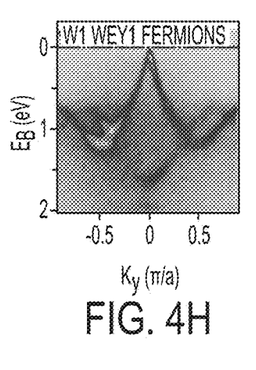
FIGS. 4H and 4I shows an ARPES E-$k_y$ dispersion map and its zoomed-in version along the Cut 3 direction, respectively, revealing the linearly dispersive W1 Weyl cone.
Figure 4I:
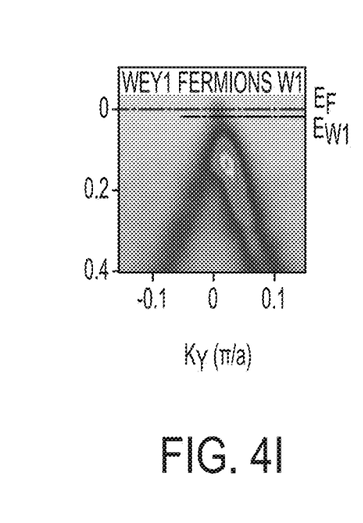
Figure 4J:
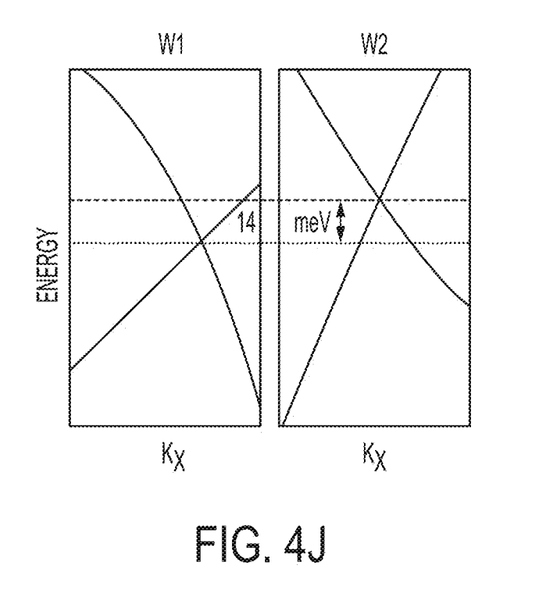
FIG. 4J shows a first-principles calculation shows a 14 meV energy difference between the W1 and W2 Weyl nodes.

Bulk sensitive SX-ARPES data reveal the existence of bulk Weyl cones and Weyl nodes. FIGS. 4A-4J show observations of bulk Weyl Fermion cones and Weyl nodes in TaAs, according to examples of the present disclosure. FIGS. 4A and 4B shows first principles calculated and ARPES measured $k_z$-$k_x$ Fermi surface maps at $k_y=0$, respectively. FIG. 4C shows ARPES measured and first-principles calculated $k_x$-$k_y$ Fermi surface maps at the $k_z$ value that corresponds to the W2 Weyl nodes. The dotted line defines the k-space cut direction for Cut 1, which goes through two nearby W2 Weyl nodes along the $k_y$ direction. The black cross defines Cut 2, which means that the $k_x,k_y$ values are fixed at the location of a W2 Weyl node and one varies the $k_z$ value. FIG. 4D shows an ARPES E-$k_y$ dispersion map along the Cut 1 direction, which clearly shows the two linearly dispersive W2 Weyl cones. FIG. 4E shows an ARPES E-$k_z$ dispersion map along the Cut 2 direction, showing that the W2 Weyl cone also disperses linearly along the out-of-plane $k_z$ direction. FIG. 4F shows a first-principles calculated E-$k_z$ dispersion that corresponds to the Cut 2 shown in FIG. 4E. FIG. 4G shows an ARPES measured $k_x$-$k_y$ Fermi surface maps at the $k_z$ value that corresponds to the W1 Weyl nodes. The dotted line defines the k-space cut direction for Cut 3, which goes through the W1 Weyl nodes along the $k_y$ direction. FIGS. 4H and 4I shows an ARPES E-$k_y$ dispersion map and its zoomed-in version along the Cut 3 direction, respectively, revealing the linearly dispersive W1 Weyl cone. FIG. 4J shows a first-principles calculation shows a 14 meV energy difference between the W1 and W2 Weyl nodes.

This serves as an independent proof of the Weyl semimetal state in TaAs. FIG. 4B shows the SX-ARPES measured $k_x$-$k_z$ Fermi surface at $k_y=0$ (note that none of the Weyl nodes are located on the $k_y=0$ plane). The clear dispersion is emphasized along the $k_z$ direction (FIG. 4B) firmly shows that the SX-ARPES predominantly images the bulk bands. SX-ARPES boosts the bulk-surface contrast in favor of the bulk band structure, which can be further tested by measuring the band dispersion along the $k_z$ axis in the SX-ARPES setting. This is confirmed by the agreement between the ARPES data (FIG. 4B) and the corresponding bulk band calculation (FIG. 4A). An incident photon energy (i.e. a $k_z$ value) is chosen that corresponds to the k-space location of W2 Weyl nodes and map the corresponding $k_x$-$k_y$ Fermi surface. As shown in FIG. 4C, the Fermi points that are located away from the $k_x$ or $k_y$ axes are the W2 Weyl nodes. In FIG. 4D, two linearly dispersive cones are observed that correspond to the two nearby W2 Weyl nodes along Cut 1. The k-space separation between the two W2 Weyl nodes is measured to be 0.08 Å$^{-1}$, which is consistent with both the bulk calculation and the separation of the two terminations of the crescent Fermi arcs measured in FIGS. 3A-3G. The linear dispersion along the out-of-plane direction for the W2 Weyl nodes is shown by the data in FIG. 4E. Additionally, it was observed that the W1 Weyl cones in FIGS. 4G-4I. Notably, the data shows that the energy of the bulk W1 Weyl nodes is lower than that of the bulk W2 Weyl nodes, which agrees well with the calculation shown in FIG. 4J and an independent modeling of the bulk transport data on TaAs.

In general, in a spin-orbit coupled bulk crystal, point-like linear band crossings can either be Weyl cones or Dirac cones. Because the observed bulk cones in FIGS. 4C and 4D are located neither at Kramers' points nor on a rotational axis, they cannot be identified as bulk Dirac cones and have to be Weyl cones according to topological theories. Therefore, the SX-ARPES data alone, proves the existence of bulk Weyl nodes. The agreement between the SX-ARPES data and the bulk calculation, which only requires the crystal structure and the lattice constants as inputs, provides further cross-check.

Figure 5A:
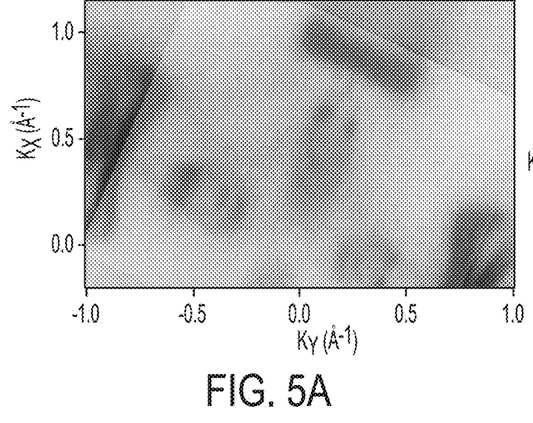
FIG. 5A shows a low-photon-energy ARPES Fermi surface map (hv=90 ev) from FIG. 3A, with the SX-ARPES map (hv=650 ev) from FIG. 4C overlaid on top of it to-scale, showing that the locations of the projected bulk Weyl nodes correspond to the terminations of the surface Fermi arcs.
Figure 5B:
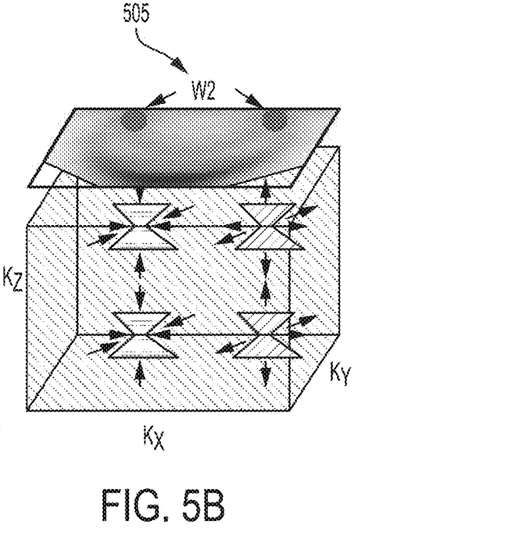
FIG. 5B shows the bottom shows a rectangular tube in the bulk BZ that encloses four W2 Weyl nodes. These four W2 Weyl nodes project onto two points at the (001) surface BZ with projected chiral charges of ±2, shown by the circles 505. The top surface shows the ARPES measured crescent surface Fermi arcs that connect these two projected Weyl nodes.
Figure 5C:
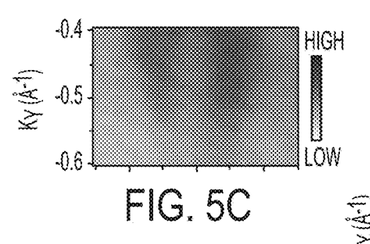
FIG. 5C shows surface state Fermi surface map at the k-space region corresponding to the terminations of the crescent Fermi arcs. The k-space region is defined by the dotted box 510 in FIG. 5E.
Figure 5D:
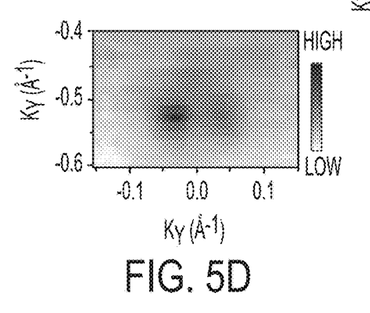
FIG. 5D shows bulk Fermi surface map at the k-space region corresponding to the W2 Weyl nodes. The k-space region is defined by the dotted box 405 in FIG. 4C.
Figure 5E:
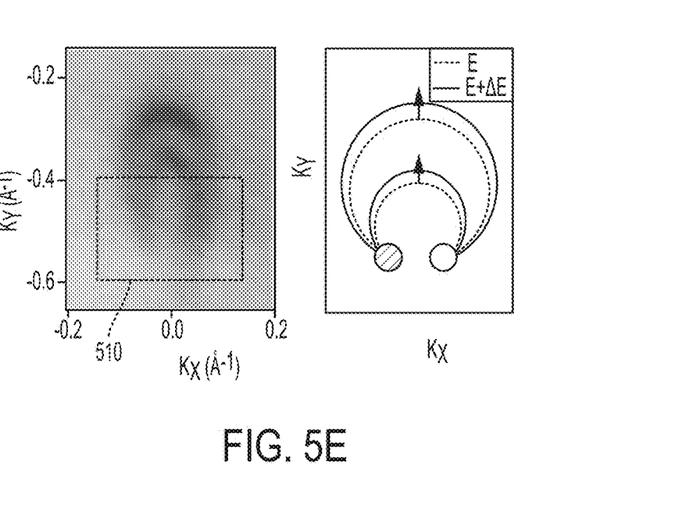
FIG. 5E shows ARPES and schematic of the crescent-shaped co-propagating Fermi arcs.

Finally, it is shown that the k-space locations of the surface Fermi arc terminations match with the projection of the bulk Weyl nodes on the surface BZ. FIGS. 5A-5E show surface-bulk correspondence and the topologically non-trivial state in TaAs, according to examples of the present disclosure. FIG. 5A shows a low-photon-energy ARPES Fermi surface map (hv=90 ev) from FIG. 3A, with the SX-ARPES map (hv=650 ev) from FIG. 4C overlaid on top of it to-scale, showing that the locations of the projected bulk Weyl nodes correspond to the terminations of the surface Fermi arcs. FIG. 5B shows the bottom shows a rectangular tube in the bulk BZ that encloses four W2 Weyl nodes. These four W2 Weyl nodes project onto two points at the (001) surface BZ with projected chiral charges of ±2, shown by the circles 505. The top surface shows the ARPES measured crescent surface Fermi arcs that connect these two projected Weyl nodes. FIG. 5C shows surface state Fermi surface map at the k-space region corresponding to the terminations of the crescent Fermi arcs. The k-space region is defined by the dotted box 510 in FIG. 5E. FIG. 5D shows bulk Fermi surface map at the k-space region corresponding to the W2 Weyl nodes. The k-space region is defined by the dotted box 405 in FIG. 4C. FIG. 5E shows ARPES and schematic of the crescent-shaped co-propagating Fermi arcs.

The SX-ARPES measured bulk Fermi surface containing W2 Weyl nodes (FIG. 4C) are superimposed onto the low-photon-energy ARPES Fermi surface containing the surface Fermi arcs (FIG. 3A) to-scale. From FIG. 5A, it can be seen that all the arc terminations and projected Weyl nodes match with each other within the k-space region that is covered in our measurements. To establish this point quantitatively, in FIG. 5C, the zoomed-in map near the crescent Fermi arc terminations are shown, from which the k-space location of the terminations are obtained to be at $\overline{k}_{arc}$=(0.04±0.01 Å$^{-1}$, 0.51±0.01 Å$^{-1}$). FIG. 5D shows the zoomed-in map of two nearby W2 Weyl nodes, from which the k-space location of the W2 Weyl nodes are obtained to be at $\overline{k}_{w2}$=(0.04±0.015 Å$^{-1}$, 0.53±0.015 Å$^{-1}$). In the bulk calculation, the k-space location of the W2 Weyl nodes is found to be at (0.035 Å$^{-1}$, 0.518Å$^{-1}$). Since the SX-ARPES bulk data and the low-photon-energy ARPES surface data are completely independent measurements using two different beamlines, the fact that they match well provides another piece of evidence of the topological nature (the surface-bulk correspondence) of the Weyl semimetal state in TaAs.

Figure 6:
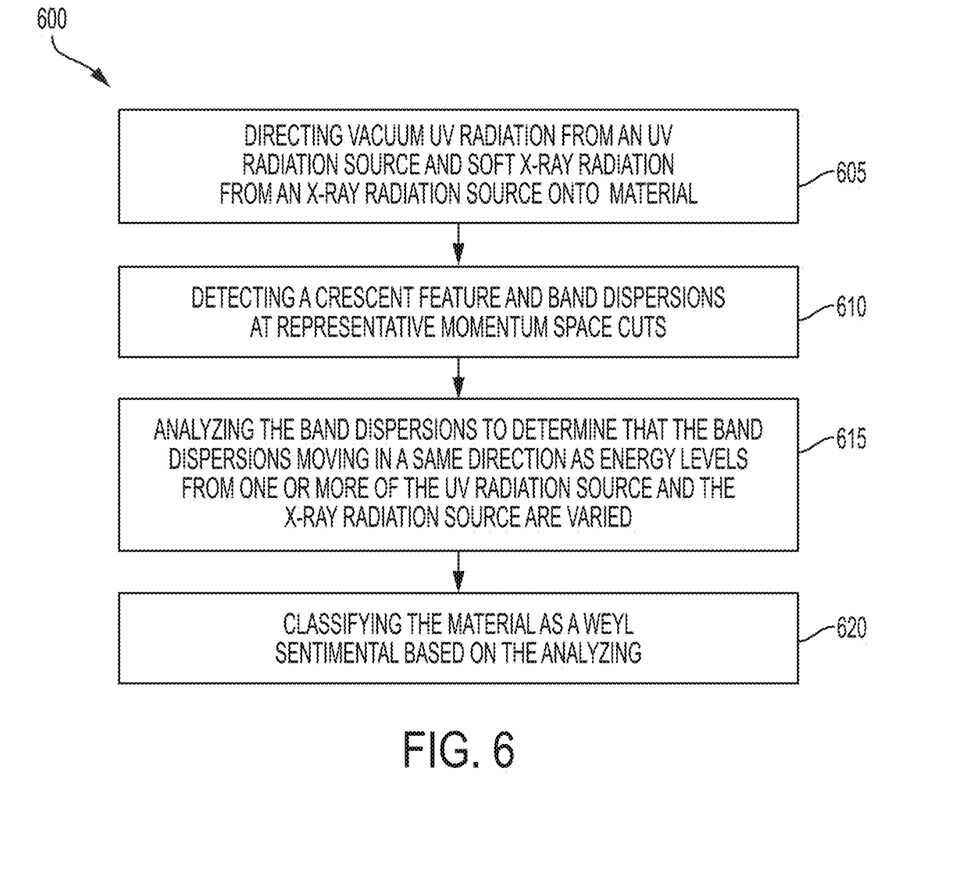
FIG. 6 shows a method of identifying a Weyl semimetal, according to example of the present disclosure.

FIG. 6 shows a method of identifying a Weyl semimetal 600, according to example of the present disclosure. At 605, UV radiation from an UV radiation source and soft x-ray radiation from an x-ray radiation source is directed onto a material. As discussed above, the UV radiation can be between about 10 eV and about 100 eV and the soft x-rays can be between about 300 eV and about 1000 eV. At 610, a crescent feature and band dispersions at representative momentum space cuts can be detected. At 615, the band dispersions can be analyzed, for example by a hardware processor that is programmed with appropriate software, to determine that the band dispersions are moving in a same direction as energy levels from one or more the of UV radiation source and the x-ray radiation source are varied. At 620, the material can be classified as a Weyl semimetal based on the analyzing.

While the present teachings have been illustrated with respect to one or more implementations, alterations and/or modifications may be made to the illustrated examples without departing from the spirit and scope of the appended claims. For example, it will be appreciated that while the process is described as a series of acts or events, the present teachings are not limited by the ordering of such acts or events. Some acts may occur in different orders and/or concurrently with other acts or events apart from those described herein. Also, not all process stages may be required to implement a methodology in accordance with one or more aspects or embodiments of the present teachings. It will be appreciated that structural components and/or processing stages may be added or existing structural components and/or processing stages may be removed or modified.

Further, one or more of the acts depicted herein may be carried out in one or more separate acts and/or phases. Furthermore, to the extent that the terms "including," "includes," "having," "has," "with," or variants thereof are used in either the detailed description and the claims, such terms are intended to be inclusive in a manner similar to the term "comprising." The term "at least one of" is used to mean one or more of the listed items may be selected. As used herein, the phrase "one or more of", for example, A, B, and C means any of the following: either A, B, or C alone; or combinations of two, such as A and B, B and C, and A and C; or combinations of three A, B and C.

The term "about" indicates that the value listed may be somewhat altered, as long as the alteration does not result in nonconformance of the process or structure to the illustrated embodiment. Finally, "exemplary" indicates the description is used as an example, rather than implying that it is an ideal.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed:

1. A method of producing a Weyl semimetal, the method comprising:
   selecting a pair of materials from the group consisting of: tantalum (Ta), arsenide (As), niobium (Nb), and phosphide (P), wherein each of the pair of materials is in powder form and has an initial purity of at least 99.9%;
   heating the pair of selected materials to form a polycrystalline compound;
   sealing the polycrystalline compound and a transfer agent in a first end of a closed ampule; and
   heating the closed ampule to a first temperature at the first end and to a second temperature at a second end to produce a temperate gradient along a length of the closed ampule to grow the Weyl semimetal via a chemical vapor transport (CVT) reaction, wherein the first temperature is lower than the second temperature.

2. The method of claim 1, wherein the heating the pair of selected materials, further comprises:
   depositing the pair of materials into a container composed of silica;
   evacuating the container in vacuum;
   heating the container except where the two materials are located to reduce bound water from an inner wall of the container; and
   fluxing and evacuating the container with argon gas of purity of about 99.999% and sealing the container with an inner residue pressure less than 1 Pa.

3. The method of claim 2, further comprising, subsequent to the sealing the container, heating the container at a third temperature for a first time period and then heating the container at a fourth temperature that is higher than the third temperature for a second time period.

4. The method of claim 3, wherein the fourth temperature is chosen to be high for thermal decomposition of impurities while preventing possible reaction between the inner wall of the container and one or more of the two materials.

5. The method of claim 3, wherein the third temperature is about 873K and the first time period is about 36 hours, the container is heated to the fourth temperature of about 1323K over a 50 hours, and kept at the fourth temperature at the second time period of 36 hours.

6. The method of claim 1, wherein the transfer agent is one or more of:
$SnI_4$ and $TeI_4$.

7. The method of claim 1, wherein a mass of the transfer agent is between approximately 15% and 30% of a mass of the pair of materials.

8. The method of claim 1, wherein the CVT occurs over about 7 days.

9. The method of claim 1, wherein the first temperature is about 1073K and the second temperature is about 1273K.

10. A method of producing a TaAs Weyl semimetal, the method comprising:
providing a tantalum (Ta) powder and an arsenic (As) powder, wherein each of the Ta powder and the As powder has an initial purity of at least 99.9%;
heating the Ta powder and the As powder to form a polycrystalline TaAs compound, wherein heating eliminates a presence of $TaAs_2$;
sealing the polycrystalline TaAs compound and a transfer agent in a first end of a closed ampule, wherein the transfer agent is one or more of: $SnI_4$ and $TeI_4$; and
heating the closed ampule to about 1073K at the first end and to about 1273K at a second end to produce a temperate gradient along a length of the closed ampule to grow the TaAs Weyl semimetal via a chemical vapor transport (CVT) reaction.

11. The method of claim 10, wherein heating the Ta and As, further comprises:
depositing the Ta powder and the As powder into a container composed of silica;
evacuating the container in vacuum;
heating the container except where the Ta powder and the As powder are located to reduce bound water from an inner wall of the container; and
fluxing and evacuating the container with argon gas of purity of about 99.999% and sealing the container with an inner residue pressure less than 1 Pa.

12. The method of claim 11, further comprising, subsequent to the sealing the container, heating the container to about 873K for about 36 hours and then heating the container to about 1323K over 50 hours and kept at about 1323K for about 36 hours.

13. The method of claim 10, wherein the CVT occurs over about 7 days.

14. A method of identifying a Weyl semimetal, the method comprising:
directing vacuum ultraviolet (UV) radiation from an UV radiation source and soft x-ray radiation from an x-ray radiation source onto a material;
detecting a crescent feature and band dispersions at representative momentum space cuts;
analyzing, using a hardware processor, the band dispersions to determine that the band dispersions moving in a same direction as energy levels from one or more the of UV radiation source and the x-ray radiation source are varied; and
classifying the material as a Weyl semimetal based on the analyzing.

15. The method of claim 14, wherein the UV radiation source uses low-photon energy angle-resolved photoemission spectroscopy ("ARPES").

16. The method of claim 15, wherein the analyzing further comprising tuning free parameters of a surface calculation to obtain a calculated surface Fermi surface, wherein a Weyl semimetal exists if the calculated surface Fermi surface reproduces data from the ARPES.

17. The method of claim 14, wherein the UV radiation is between about 10 eV and about 100 eV and the soft x-ray radiation is between about 300 eV and about 1000 eV.

18. The method of claim 14, wherein the analyzing further comprises:
mapping a $k_x$-$k_z$ Fermi surface using the ARPES;
identifying a bulk band structure;
selecting an incident photo energy that corresponds to the k-space location of nodes located away from a $k_z$=0 plane;
mapping a $k_x$-$k_y$ Fermi surface; and
identifying a Fermi point comprising a dispersive cone away from $k_x$ or $k_y$ axes;
wherein a Weyl semimetal exists if the Fermi point away from the $k_x$ or $k_y$ axes exist.

19. The method of claim 18, wherein the classifying further comprises comparing a location of the Fermi point with bulk calculations, wherein a Weyl semimetal exists it the location of the Fermi point is consistent with bulk calculations.

* * * * *